(12) United States Patent
Barsky et al.

(10) Patent No.: US 6,514,695 B1
(45) Date of Patent: Feb. 4, 2003

(54) COMPOSITIONS AND METHODS FOR INTRADUCTAL GENE THERAPY

(75) Inventors: Sanford H. Barsky, Los Angeles, CA (US); Mary L. Alpaugh, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/488,464

(22) Filed: Jan. 20, 2000

Related U.S. Application Data

(60) Provisional application No. 60/116,470, filed on Jan. 20, 1999.

(51) Int. Cl.[7] .......................... C12Q 1/68; C12N 15/63; C12N 15/85; C07H 21/04
(52) U.S. Cl. ...................... 435/6; 435/320.1; 435/455; 536/23.1
(58) Field of Search ..................... 435/6, 320.1, 455; 514/44; 536/23.1

(56) References Cited

U.S. PATENT DOCUMENTS 5,763,415 A * 6/1998 Sukumar ..................... 514/44

OTHER PUBLICATIONS

Wolff et al. Ex vivo breast cancer cell purging by adenovirus–mediated cytosine deaminase gene transfer and short-–term incubation with 5–fluorocytosine completely prevents tumor growth after transplantation. Human Gene Therapy vol. 9:2277–2284., 10–10.*

Garcia–Sanchez et al. Cytosine deaminase adenoviral vector and 5–fluorocytosine selectively reduce breast cancer cells 1 million fold when they contaminate hematopoietic cells: A potential purging method for autologous transplantation. Blood. vol. 92(.*

McKenzie et al. Breat cancer prevention through the targeted destruction of breast epithelial cells. Proc. Am Assoc. for Ca Res. vol. 38(0):p207. Apr. 1997.*

Summerford et al. Membrane–associated heparan sulfate proteoglycan is a receptor or adeno–associated virus type 2 virions. J. Virol. vol. 72(2):1438–1445. Feb. 1998.*

Gomm et al. A paracrine role for myoepithelial cell–derived FGF2 in the normal human breast. Exp. Cell. Res. vol. 234(1):165–173. Jun. 1997.*

Alpaugh, M.L. et al., "Use of rAd and rAAV to selectively target breast epithelium and myoepithelium of breast cancer prophylaxis", *Proceedings of the American Association for Cancer Research Annual*, vol. 40, Mar. 1999, XP001063189, 90th Annual Meeting of the American Association for Cancer Research, Philadelphia, Pennsylvania, USA, Apr. 10–14, 1999, Mar. 1999, abstract.

Alpaugh, M.L. et al., "A nipple ductal orifice approach to adenoviral gene therapy and prophylaxis",*Modern Pathology*, vol. 12, No. 1, Jan. 1999, p. 15A, XP001022535, Annual Meeting of the United States and Canadian Academy of Pathology, San Francisco, California, USA, Mar. 20–26, 1999, abstract.

Bergelson, Jeffrey M. et al., "The murine CAR homolog is a receptor for coxsackie B viruses and adenoviruses", *Journal of Virology*, vol. 72, No. 1, Jan. 1998, pp. 415–419, XP002195888.

Chen, L. et al., "Breast Cancer Selective Gene Expression and Therapy Mediated by Recombinant Adenoviruses Containing the DF3MUC1 Promoter", *Journal of Clinical Investigation*, New York, NY, USA, Vo. 96, No. 6, pp. 2775–2782, CP002071017.

Colak, A. et al., "Adenovirus–Mediated Gene Therapy in an Experimental Model of Breast Cancer Metastatic to the Brain", *Human Gene Therapy*, vol. 6, No. 10, Oct. 1995, pp. 1317–1322, XP001068644.

Duan, D. et al., "Polarity Influences the Efficiency of Recombinant Adenoassociated Virus Infection in Differentiated Airway Epithelia", *Human Gene Therapy*, vol. 9, No. 18, Dec. 10, 1998, pp. 2761–2776, XP000828295.

Ealovega, M. et al., "bcl–xs Gene Therapy Induces Apoptosis of Human Mammary Tumors in Nude Mice", *Cancer Research*, vol. 56, May 1, 1996, pp. 1965–1969, XP001063183.

Hemmi, S. et al., "The presence of human coxsackievirus and adenovirus receptor is associated with efficient adenovirus–mediated transgene expression in human melanoma cultures", *Human Gene Therapy*, vol. 9, No. 16, Nov. 1, 1998, pp. 2363–2373, XP001068738.

Pope, I.M. et al., "The Role of the Bystander Effect in Suicide Gene Therapy", *European Journal of Cancer*, Pergamon Press, Oxford, GB, vol. 33, No. 7, Jun. 1997, pp. 1005–1016, XP004282795.

Yang, Jason et al., "Adenoviral–mediated gene transfer into primary human and mouse mammary epithelial cells in vitro and in vivo", *Cancer Letters*, vol. 98, No. 1, 1995, pp. 9–17, XP002195881.

Katayose, Dai et al., "Cytotoxic Effects of Adenovirus–Mediated Wild–Type p53 Protein Expression in Normal and Tumor Mammary Epithelial Cells," *Clinical Cancer Research*, Aug. 1995, vol. 1, pp. 889–897.

(List continued on next page.)

*Primary Examiner*—Terry McKelvey
*Assistant Examiner*—William Sandals
(74) *Attorney, Agent, or Firm*—Gates & Cooper LLP

(57) ABSTRACT

The present invention provides methods for the selective transduction of a cell in a ductal system in a mammary gland by contacting, via ductal cannulation, the cell with a vector that selectively targets the cell. In this context, the invention provides prophylactic and therapeutic methods of treating the ductal epithelium of the breast, for disease, in particular cancer. The present invention further provides diagnostic methods of determining the presence of disease in the ductal epithelium of the breast, in particular cancer.

12 Claims, 8 Drawing Sheets

OTHER PUBLICATIONS

Wolff, Gerhard et al., "*Ex Vivo* Breast Cancer Cell Purging by Adenovirus–Mediated Cytosine Deaminase Gene Transfer and Short–Term Incubation with 5–Fluorocytosine Completely Prevents Tumor Growth after Transplantation," *Human Gene Therapy*, Oct. 10, 1998, vol. 9, pp. 2277–2284.

M.D. Sternlicht et al. (1996) "Characteristics of the Extracellular Matrix and Proteinase Inhibitor Content of Human Myoepithelial Tumors" Laboratory Investigation 74(4):781–796.

M.D. Sternlicht et al. (1997) "The myoepithelial defense: a host defense against cancer" Medical Hypotheses 48(1):37–46.

C. Summerford et al. (1998) "Membrane–Associated Heparan Sulfate Proteoglycan Is a Receptor for Adeno–Associated Virus Type 2 Virions" Journal of Virology pp. 1438–1445, vol. 72(2).

M. Nguyen et al. (1996) "An Update on Core Needle Biopsy for Radiologically Detected Breast Lesions" Cancer, pp 2340–2345, vol. 78.

S.M. Love et al. (1996) "Breast–duct endoscopy to study stages of cancerous breast" 348(9033):997–999.

J.M. Bergelson et al. (1997) "Isolation of a Common Receptor for Coxsackie B Viruses and Adenoviruses 2 and 5" Science 275(5304):1320–1323.

Shao, Zhi–Ming et al., "The Human Myoepithelial Cell Exerts Antiproliferative Effects on Breast Carcinoma Cells Characterized by p21WAF1/CIP1 Induction, G2/M Arrest, and Apoptosis", *Experimental Cell Research*, vol. 241, No. 2, Jun. 15, 1998, pp. 394–403.

Seftor, R. E. B. et al., "Maspin Suppresses the Invasive Phenotype of Human Breast Carcinoma", *Cancer Research*, vol. 24, No. 58, Dec. 15, 1998, pp. 5681–5685.

\* cited by examiner

COMPOSITIONS AND METHODS FOR INTRADUCTAL GENE THERAPY

This application claims the benefit of U.S. provisional patent application Serial No. 60/116,470, filed Jan. 20, 1999. The entire contents of this provisional patent application is incorporated by reference into this application.

This invention was made with Government support under U.C. Biostar Biotechnology grant S98-42, grant No. BC990959, awarded by the Department of Defense Breast Cancer Research Program and grant No. DAMD 17-96-C6117, awarded by the Department of the Army, U.S. Army Medical Research Acquisition Activity. The government has certain rights in this invention.

FIELD OF THE INVENTION

The present invention relates to the use of cell specific vectors in the diagnosis as well as the prophylactic and therapeutic treatment of diseases of the breast, in particular cancer.

BACKGROUND OF THE INVENTION

Cancers of the breast are one of the leading causes of death among women, with the cumulative lifetime risk of a woman developing breast cancer estimated to be 1 in 9. Consequently, understanding the origins of these malignancies as well as the identification of new therapeutic modalities is of significant interest to health care professionals.

The mature human breast comprises from six to nine major ducts, which emanate from the nipple, serially branch into ducts and terminate in lobuloalveolar structures (Russo et al., Lab. Invest. 62(3): 244–278 (1990)). The branching network of ducts is composed of luminal epithelial cells in a supporting matrix of connective tissue and myoepithelial cells. Tissues removed from the human female breast during surgery and autopsy have been examined in numerous studies directed at the nature and site of origin of neoplastic growth. Subgross sampling and histological confirmation have enabled pathological characterization of entire breasts which shows that human breast cancer arise within the ductal system of the breast exclusively from luminal epithelial cells. Ductal origin is supported by the presence of more extensive epithelial proliferations, which are presumed to be preneoplastic, in surgically removed cancerous breasts as compared to nonmalignant breasts removed during autopsies.

With the significant cumulative lifetime risk of a woman developing breast cancer, there is an urgent need to develop both therapeutic methods of treatment that are more effective, less invasive and accompanied by fewer side effects as well as prophylactic methods of treatment that are more effective than increased and intensified physical monitoring and far less extreme than radical mastectomy. In spite of the recent discovery of the heritable breast cancer susceptibility loci including BRCA1 and other genes (see e.g. Miki et al., Science 266:66–71 (1994)), and the increasing ability of physicians to identify women with elevated breast cancer risk, prophylactic methods are still currently limited to physical monitoring and prophylactic mastectomy.

In view of the above, what is needed in the art is the identification of novel methods which aid in the prevention and treatment of cancers of the mammary gland. In this context, optimal methods are those which have a wide application both in the diagnosis of cancer, as well as the prophylactic and therapeutic treatment of cancer.

SUMMARY OF THE INVENTION

The present invention is based on the observations of the respective roles of the epithelial and myoepithelial cell lineages in the development of breast cancer and the fact that these cell types differentially express gene products that can be targeted by cell specific vectors. In this context, new strategies emerge which can be used as a means of breast carcinoma diagnosis, prophylaxis and treatment. A first strategy is to selectively target cells of the breast epithelium so that breast carcinoma does not develop. A second strategy is to target myoepithelial cells as a means of bolstering the myoepithelial defense so that even if DCIS develops, it will be confined to the ductal system indefinitely.

The present invention provides prophylactic and therapeutic methods of treating a disease of the ductal epithelium of the mammary gland, in particular cancer. The present invention further provides diagnostic methods of assessing the status of cancers of the mammary gland. In this context, the present invention provides methods directed to selectively transducing a cell in a ductal system in a mammary gland comprising the step of using ductal cannulation to contact the cell with a vector that selectively targets that cell. In an illustrative embodiment, the invention consists of a method of selectively transducing either a epithelial cell or a myoepithelial cell, by contacting the cell with a vector that selectively targets a CAR molecule that is expressed on the epithelial cell or a heparin sulfate proteoglycan molecule that is expressed on the myoepithelial cell.

In a specific embodiment of the invention, the vector is a replication defective adenovirus which targets a molecule expressed solely by a epithelial cell and subsequently induces cell death by delivery of an cytolysis inducing gene such as thymidine kinase or cytosine deaminase. In a more preferred embodiment, the vector is a replication-competent lytic adenovirus which targets a coxsackievirus and adenovirus receptor (CAR) molecule expressed by the epithellal cell and subsequently induces cell death by lysis. In a highly preferred embodiment, the replication-competent lytic adenovirus contains a cis element such as a lactoalbumin promoter and the MUCI promoter which stimulates adenovirus replication in the presence of a trans factor present in the epithelial cell and induces more effective lysis. The myoepithelial cells of the breast duct, which lack CAR expression (as shown, for example by RT-PCR), are completely resistant to adenovirus infection (transduction) and serve as a barrier to systemic infection.

In another specific embodiment of the invention, the vector is a recombinant adeno-associated virus which targets a molecule expressed by a myoepithelial cell and comprises a polynucleotide which encodes a polypeptide which inhibits the development of epithelial cell cancer. In a specific embodiment, the polypeptide of the recombinant adeno-associated virus inhibits angiogenesis or the proliferation, invasion or metastases of a epithelial cell. In a specific embodiment, the polypeptide is maspin, thrombospondin-1, TIMP-1, protease nexin-II, $\alpha$-1 antitrypsin or soluble bFGF receptor. In a more preferred embodiment, the recombinant adeno-associated virus contains a cis element such as a lactoalbumin promoter and the MUCI promoter which stimulates recombinant adeno-associated virus replication in the presence of a trans factor present in the epithelial cell.

The present invention also provides a method of treating the ductal epithelium of a mammary gland prophylactically for cancer, which method comprises the step of contacting, by ductal cannulation, the ductal epithelium of the mammary gland with a tissue specific vector so as to inhibit the formation of cancer of ductal epithelial origin. In addition, the present invention provides combined therapeutic/prophylactic methods of treating the mammary gland therapeutically by surgery, radiation and/or chemotherapy and, either concomitantly or subsequently, contacting the ductal epithelium of the mammary gland with a cell specific vector which specifically targets a epithelial or a myoepithelial cell.

The present invention also provides a method of determining the lineage of a cell in a ductal system in a mammary gland selected from the group consisting of a luminal epithelial cell and a myoepithelial cell, by using ductal cannulation to contact the cell with vector containing a reporter gene, wherein the vector selectively targets a molecule that is expressed on the epithelial cell or the myoepithelial cell.

In addition, the present invention provides compositions including recombinant adenovirus and recombinant adeno-associated virus vectors as well as myoepithelial cell lines and transplantable xenografts.

DETAILED DESCRIPTION OF THE INVENTION

Definitions

Figure 1:
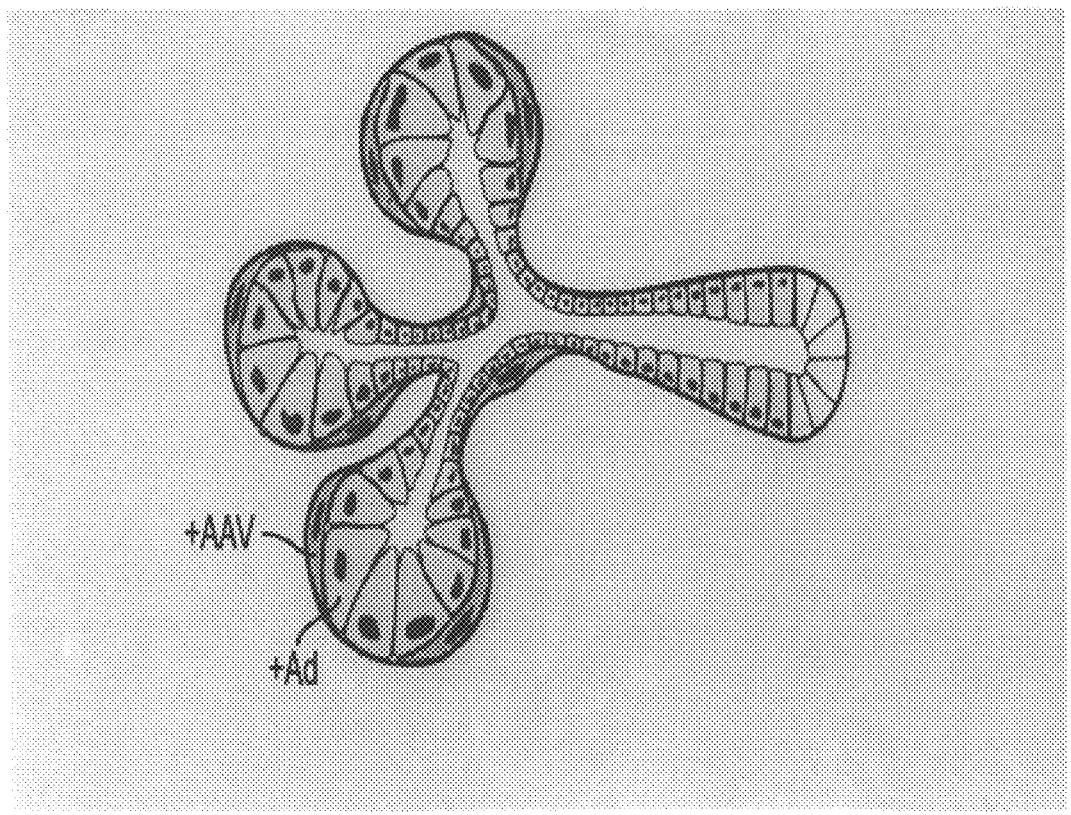
FIG. 1 is a schematic which depicts the ductal-lobular unit of the breast and illustrates the possibility of gene therapy strategies targeting either epithelial cells and/or myoepithelial cells.
Figure 2A:
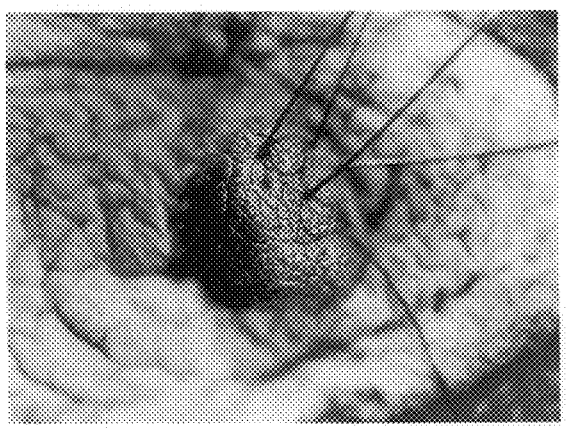
FIGS. 2A is a photograph illustrating the feasibility of gaining access to the entire ductal system of the breast through nipple duct identification and cannulation.
Figure 2B:
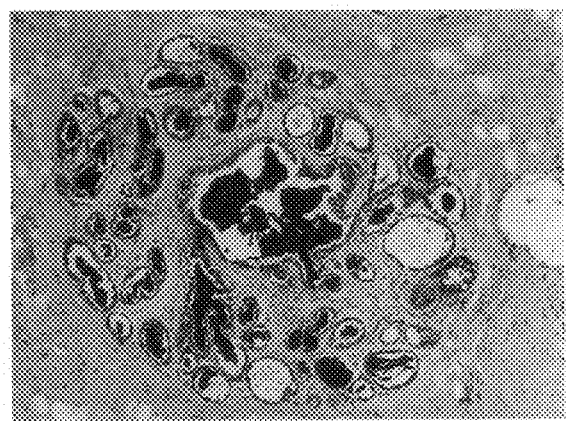
FIG. 2B, a photograph showing that when nipple ducts are individually cannulated, an injected dye reaches every ductal orifice.

The term "transduce" is used in its broadest sense and refers to a process wherein a vector gains entry in to a cell so that polynucleotides of the vector are delivered to the cell.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. eucaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Lining may be accomplished by ligation at convenient restriction sites. If such sites do not exist, the synthetic oligonucleotide adaptors or linkers maybe used in accordance with conventional practice.

"Polynucleotide" and "nucleic acid" refer to single- or double-stranded molecules which may be DNA, comprised of the nucleotide bases A, T, C and G, or RNA, comprised of the bases A, U (substitutes for T), C, and G. The polynucleotide may represent a coding strand or its complement. Polynucleotide molecules may be identical in sequence to the sequence which is naturally occurring or may include alternative codons which encode the same amino acid as that which is found in the naturally occurring sequence (See, Lewin "Genes V" Oxford University Press Chapter 7, pp. 171–174 (1994)). Furthermore, polynucleotide molecules may include codons which represent conservative substitutions of amino acids as described. The polynucleotide may represent genomic DNA or cDNA.

"Polypeptide" refers to a molecule comprised of amino acids which correspond to those encoded by a polynucleotide sequence which is naturally occurring. The polypeptide may include conservative substitutions where the naturally occurring amino acid is replaced by one having similar properties, where such conservative substitutions do not alter the function of the polypeptide (See, Lewin "Genes V" Oxford UniversityPress Chapter 1, pp.: 9–13 (1994)).

The gene therapy strategies provided herein are predicated on either selectively destroying the breast epithelial cell (where cancers arise) and/or enhancing the functions of the myoepithelial cell (which are natural cancer suppressors). The present invention utilizes observations of the different of the ductal epithelial and ductal myoepithelial cell lineages in the development of breast cancer and the fact that these cell types differentially express gene products that can be targeted by cell specific vectors. In this context, new strategies emerge which can be used as a means of breast carcinoma diagnosis, prophylaxis and treatment. A first strategy is to selectively transduce luminal epithelium cells so that breast carcinoma does not develop. A second strategy is to selectively transduce myoepithelial cells as a means of bolstering the myoepithelial defense so that even if DCIS develops, it will be confined to the ductal system indefinitely.

The present invention takes advantage of observations that early breast cancer can be thought of as a disease of the ductal system which arises from ductal epithelium and that human breast cancer arises within the ductal system of the breast exclusively from epithelial cells that are located within the breast duct. Throughout this application, the epithelial cells from the breast duct are referred to by a variety of art accepted designations such as ductal epithelial cells, acinar epithelial cells, luminal epithelial cells etc. (see e.g. Virchows et al., Arch. 391(1): 45–51 (1981); Cristov et al., Am. J. Pathol. 138(6): 1371–7 (1991); Lochter, Biochem. Cell Biol. 76(6): 997–1008 (1998); Lakhani et al., J. Pathol. 189(4): 496–503 (1999)) The various designations are used for purposes of clarity in the context in which they are discussed and all refer to epithelial cells which can be selectively transduced by vectors which target CAR expressed by these cells. Preferably, such cells reside within the breast duct system. When cancer is confined by this system it is termed ductal carcinoma in situ or DCIS. Recent evidence suggests that the determinants of the progression of DCIS to invasive cancer are epigenetic rather than genetic and consist of strong paracrine regulation by neighboring myoepithelial cells (T. Kuukasjarvi et al. (1997) Am. J. Pathol., 150:1465–1471). Myoepithelial cells are cells which surround this ductal system and keep the developing cancer termed ductal carcinoma in situ (DCIS) confined. Because of their close proximity, myoepithelial cells would be anticipated to exert important paracrine influences on DCIS progression. Myoepithelial cells accomplish this by their production and secretion of a number of proteinase inhibitors.

Myoepithelial cells of the breast differ from luminal ductal and acinar epithelial cells in many ways: they lack expression of the common hormonal receptor, ER-I, and its responsive genes like PR; they lie next to the basement membrane and contribute to the synthesis of that structure; they rarely transform or proliferate and when they do give rise to only low grade benign neoplasms M. D. Sternlicht and S. H. Barsky (1997) Medical Hypotheses, 48:37–46). Myoepithelial cells are ubiquitously present in normal ducts, benign proliferations such as adenosis and precancerous proliferations, e.g. DCIS. These cumulative studies suggest that DCIS is cancer of the breast in the true genetic, biological and clinical sense of the word but is limited within the confines of the ductal system by myoepithelial cells. Both epithelial cells and myoepithelial cells can then be targets of intraductal gene therapy provided that specific vectors can be identified which will selectively target each cell type.

The findings disclosed herein allow specific gene therapy approaches to carry out the strategies discussed above. A first finding is that it is possible to gain access to the entire ductal system of the breast through nipple duct identification and cannulation. A second finding is that primary mammary ductal epithelial cells express the coxsackievirus-Ad receptor (CAR, see e.g. J. Bergelson et al. (1997) Science 275:1320–1323) and are easily transduced with vectors that gain entry to the cell via CAR mediated uptake (such as certain adenovirus groups) whereas myoepithelial cells lack CAR and are completely resistant to transduction by vectors which target this molecule. As illustrated in Table I below, a third finding is that myoepithelial cells, do not express CAR and instead express cell surface heparin sulfate proteoglycan (see e.g. Summerford et al., J. Virol. 72(2), 1438–1445 (1998)) and are easily transduced with vectors that gain entry to the cell via heparin sulfate proteoglycan mediated uptake such as rAAV) whereas primary ductal epithelial cells do not express this proteoglycan and are resistant to transduction by vectors which target this molecule. These findings are supported by a number of experiments with established myoepithelial xenografts and cell lines (both immortalized and in limited short term passage), which further demonstrate the selectiveness of the rAAV for the myoepithelial target.

Table 1 depicts high cell surface heparin sulfate proteoglycan content of myoepithelial cells (HMS-1)

|  | Uronic Acid[b] | | Glycosaminoglycan Content (%) | | | | |
| --- | --- | --- | --- | --- | --- | --- | --- |
|  | (dry wt) | (DNA) | CS | HA | HS | DS | KS |
| Normal salivary gland | 1.83 | 0.031 | 4 | 56 | 24 | 16 | 0 |
| Basal cell adenoca (HMS-1) | 0.63 | 0.008 | 32 | 12 | 24 | 0 | 32 |
| Basal cell adenoca (HMS-X) | 10.45 | 0.530 | 78 | 12 | 8 | 2 | 0 |
| Adenoidcystic Ca (HMS-3X) | 8.96 | 0.298 | 77 | 11 | 9 | 3 | 0 |
| Pleomorphic adenoma | 26.49 | 3.718 | 89 | 7 | 0 | 4 | 0 |
| Squamous cell Ca (A253) | 0.77 | 0.009 | 19 | 59 | 14 | 8 | 0 |
| Squamous cell Ca (A253-X) | 3.93 | 0.094 | 30 | 27 | 31 | 12 | 0 |
| Murine EHS tumor | 7.62 | 0.356 | 0 | 6 | 94 | 0 | 0 |
| Cartilage | ND | ND | 61 | 15 | 3 | 21 | 0 |

All data represent mean values obtained from two or more determinations from the same sample.
Uronic acid was measured in micrograms per milligram of tissue (dry weight) and micrograms per microgram of DNA. CS, chondroitin sulfate: HA, hyaluronic acid; HS, heparin sulfate; DS, dermatan sulfate; KS, keratin sulfate; not determined.

The findings disclosed herein illustrate the feasibility of, using an intraductal approach and different cell specific viral vectors such as rAd, selectively targeting and destroying the breast epithelium in vivo while sparing the underlying myoepithelium Further, these findings illustrate the feasibility of, using an intraductal approach and different viral vectors such as rAAV, selectively targeting the myoepithelium in vivo with a vector containing a molecule capable of inhibiting epithelial luminal cell growth and invasion as a means of bolstering the suppressive effects of these cells. In addition, these findings allow for the utilization of replication-defective rAd and rAAV containing reporter genes in diagnostic studies which evaluate the expansion of a specific cell type. While various embodiments of the methods disclosed herein can be used to treat any exocrine gland, they are particularly useful in the treatment of the mammary gland.

The methods disclosed herein overcome a number of limitations of methods known in the art. Specifically, while a number of vectors (e.g. vaccinia, sindbis and certain adenoviral and retroviral vectors) exhibit a wide tissue tropism and are used to transduce a variety cell lineages including epithelial and myoepithelial cells, the broad specificity of these vectors can also limit their usefulness. In particular, while vectors having a wide tissue tropism are favored in certain contexts, this property is disadvantageous in situations where it is desirable to selectively transduce a specific cell lineage that is present in a mixed population of different cell lineages. For example, practitioners using vectors having a wide tissue tropism in vivo may be forced to use them only in contexts where a host's rapid immunological response will prevent them from escaping the milieu in to which they are introduced. The vectors and methods disclosed herein overcome such problems by allowing the artisan to selectively transduce a specific lineage (such as epithelial or myoepithelial cells) that is present within a mixed population of cells of different lineages. Specifically, methods utilizing vectors which selectively transduce a specific lineage restrict the ability of such vectors to gain entry into proximal cells of different lineages (which are not transduced by the vector), and consequently inhibit such vectors from escaping the milieu in to which they are introduced.

Vectors which Selectively Transduce Epithelial Cells

A significant feature of the methods of the invention disclosed herein is the identification and utilization cell specific vectors which have the ability to selectively transduce epithelial cells and not transduce myoepithelial cells. Specifically, as these vectors gain entry into target cells via a molecule which is expressed on epithelial but not myoepithelial cells, they can be used to selectively transduce epithelial cells within a mixed population of epithelial and myoepithelial cells.

A variety different vectors which gain entry into cells through the CAR molecule can be used to selectively transduce epithelial cells. Strains of the coxsackie B viruses (such as coxsackie B3 and B4) for example enter cells via CAR mediated uptake (see e.g. Bergelson et al., J. Virol. 72(1), 415–419 (1998)). Therefore, coxsackie virus vectors can be used to selectively transduce an epithelial cell in a ductal system in a mammary gland that expresses CAR molecules. In addition, certain subgroups of adenovirus also gain entry into cells via CAR. In particular, adenovirus serotypes from subgroups A (e.g. Ad12), C (e.g. Ad1, Ad2, Ad5 and Ad6), D (e.g. Ad9, Ad15, Ad30 and Ad37), E (e.g. Ad4), and F (e.g. Ad40 and Ad41) all use CAR as a cellular fiber receptor (see e.g. Roelvink et al., J. Virol. 72(10): 7909–7915 (1998)). It is however important to note that adenoviruses can target different molecules expressed by target cells and that not all adenovirus strains can be used to selectively transduce CAR expressing epithelial cells (see e.g. Nalbantoglu et al., Hum. Gene Ther. 10(6): 1009–1019 (1999). For example, subgroup B adenoviruses (e.g. Ad3, Ad7 and Ad35) appear to interact with target cells through a different cellular receptor than CAR and may not function in the disclosed methods (see e.g. Stevenson et al., J. Virol. 69(5): 2850–2857 (1995)). Therefore it is important to establish that any vector (adenovirus or otherwise) used in the disclosed methods can selectively transduce epithellal cells while not transducing proximal myoepithelial cells.

In addition to vectors having a natural tropism for CAR, it is known in the art that a wide variety of vectors may be constructed to target a specific molecule on a cell such as CAR. In particular, target cell specificity of delivery vectors can be provided by incorporation of a target cell specific binding domain by the use of any binding domain, which binds specifically to a binding site on the target cell (see e.g. U.S. Pat. No. 5,834,589 incorporated herein by reference). Because the CAR binding adenoviral fiber protein residues have been identified (see e.g. Santis et al., J. Gen. Virol. 80(Pt 6): 1519–1527 (1999)) and because the adenovirus binding activity of CAR has been localized to the amino-terminal IgV-related domain of this molecule, one skilled in the art generate target vectors specific for this binding domain.

Figure 3A:
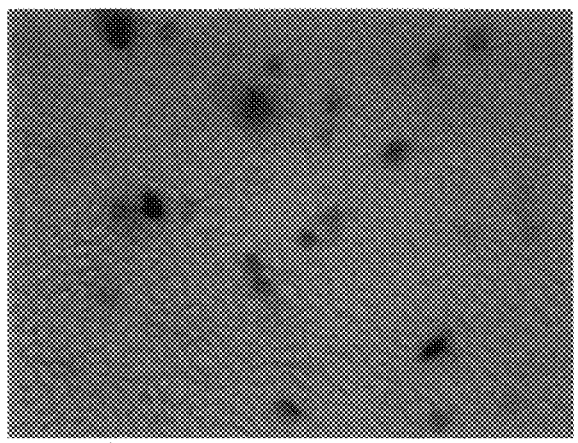
FIG. 3A is a photograph showing the absence of β-galactosidase expression in myoepithelial cells contacted with a β-galactosidase containing recombinant adenovirus (Ad2) to illustrate how the expression of CAR on the surface of epithelial cells in the ductal-lobular unit of the breast allows the selective targeting of the epithelial cells and how the absence of CAR on myoepithelial cells confers resistance of this cell to adenoviral infection.
Figure 3B:
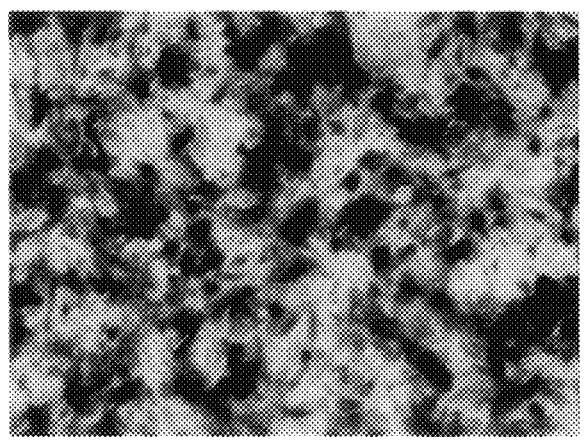
FIG. 3B is a photograph showing the intense β-galactosidase expression in epithelial cells contacted with a β-galactosidase containing recombinant adenovirus as an illustration of how the expression of CAR on the surface of epithelial cells in the ductal-lobular unit of the breast allows the selective targeting of epithelial cells.
Figure 3C:
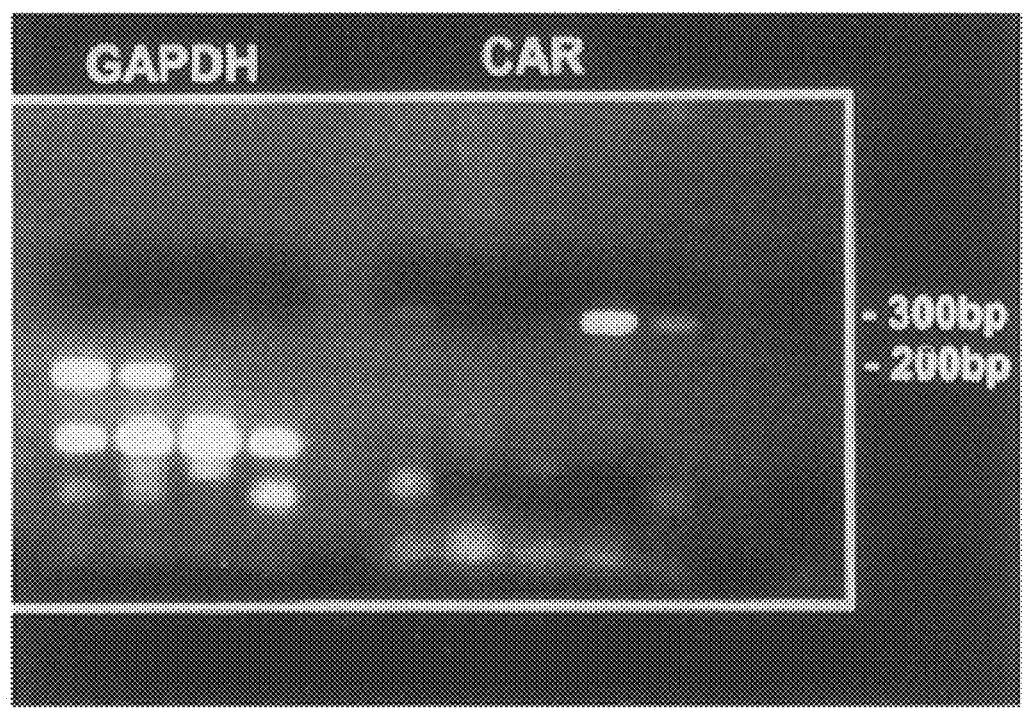
FIG. 3C is a photograph showing how CAR expression is completely absent in myoepithelial cells (lane under CAR) but present in ductal epithelial cells and carcinoma lines (other lanes).

As noted above, certain viral vectors may be able to gain entry in to cells through multiple receptors expressed on the surface of a cell. For example, certain adenoviral subtypes may be able to gain entry in to cells via the MHC class I $\alpha 2$ domain or members of the $\beta 2$ integrin family (see e.g. Davison et al., J. Virol. 73(5): 4513–4517 (1999) and Huang et al. J. Virol. 70(7): 4502–4508 (1996)). Therefore, it is important to establish that any vector (adenovirus or otherwise) used to selectively transduce epithelial cells will not transduce proximal myoepithelial cells. In particular, as certain vectors may be able to gain entry into a target cell by more than one receptor, it is prudent to assess the cellular specificity of any candidate vectors. Methods for assessing the specificity of a candidate vector are well known in the art and consist merely of contacting a target cell of interest with a candidate vector and observing if transduction occurs. In this context, FIG. 3 provides an illustrative example of an assessment of the adenoviral vector used in the disclosed examples. In particular, FIG. 3A shows the absence of $\beta$-galactosidase expression in myoepithelial cells contacted with a $\beta$-galactosidase containing recombinant adenovirus to illustrate how the expression of CAR on the surface of epithelial cells allows the selective targeting of the epithelial cells and how the absence of CAR on myoepithelial cells confers resistance of this cell to adenoviral infection. In contrast, FIG. 3B shows the intense $\beta$-galactosidase expression in epithelial cells contacted with a $\beta$-galactosidase containing recombinant adenovirus as an illustration of how the expression of CAR on the surface of epithelial cells allows the selective transduction of epithelial cells.

Vectors which Selectively Transduce Myoepithelial Cells

A significant feature of the methods of the invention disclosed herein is the identification and utilization of cell specific vectors which have the ability to selectively transduce myoepithelial cells and not transduce epithelial cells. Specifically, as these vectors gain entry into target cells via a molecule which is expressed on myoepithelial but not epithelial cells, they can be used to selectively transduce myoepithelial cells within a mixed population of myoepithelial and epithelial cells.

Different vectors which gain entry into cells through the heparin sulfate proteoglycan molecule can be used to selectively transduce myoepithelial cells. The human parvovirus, Adeno-associated virus-2 (AAV) for example can enter cells via heparin sulfate proteoglycan mediated uptake (see e.g. C. Summerford and R. J. Samulski, J. Virology 72:1438–1445)). In addition, herpesviruses are believed to target cells through their hepatin sulfate proteoglycan molecules (see e.g. Zhu et al., P.N.A.S. 92(8): 3546–3550 (1995)). It is however important to note that viral vectors can attach different molecules expressed by target cells and/or may utilize co-receptors to gain entry in to a cell (see e.g. Summerford et al., Nat. Med. 5(1): 78–82 (1999) and Qing et al., Nat. Med. 5(1): 71–11 (1999)). Therefore it is important to establish that any vector (adeno-associated virus-2 or otherwise) used in the disclosed methods can selectively transduce myoepithelial cells while not transducing proximal epithelial cells.

In addition to vectors having a natural tropism for heparin sulfate proteoglycan, it is known in the art that a wide variety of vectors may be constructed to target a specific molecule on a cell such as heparin sulfate proteoglycan. In particular, target cell specificity of delivery vectors can be provided by incorporation of a target cell specific binding domain by the use of any binding domain, which binds specifically to a binding site on the target cell (see e.g. U.S. Pat. No. 5,834,589 incorporated herein by reference).

Figure 4A:
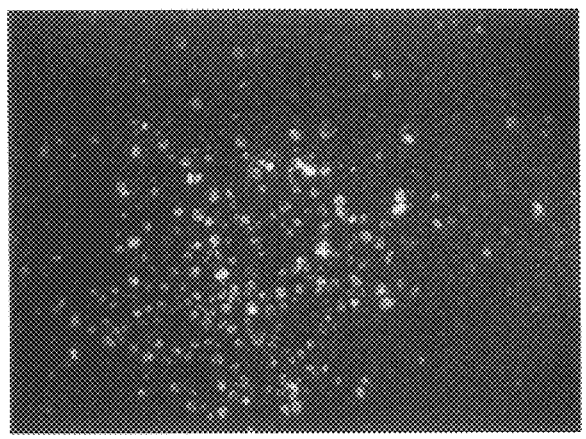
FIG. 4A is a photograph showing reporter gene expression in myoepithelial cells contacted with a recombinant adeno-associated virus containing a human green fluorescence reporter gene which illustrates how the expression of heparin sulfate proteoglycan on the surface of myoepithelial cells in the ductal-lobular unit of the breast allows the selective targeting of the myoepithelial cells.
Figure 4B:
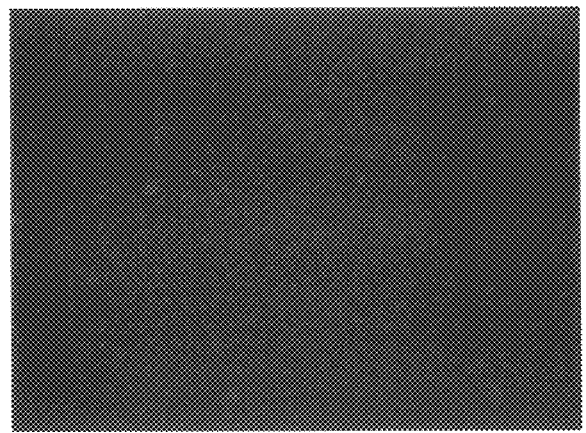
FIG. 4B is a photograph showing only background reporter gene expression in epithelial cells contacted with a recombinant adeno-associated virus containing a human green fluorescence reporter gene which illustrates how the expression of heparin sulfate proteoglycan on the surface of myoepithelial cells in the ductal-lobular unit of the breast allows the selective targeting of the myoepithelial cells.
Figure 5:
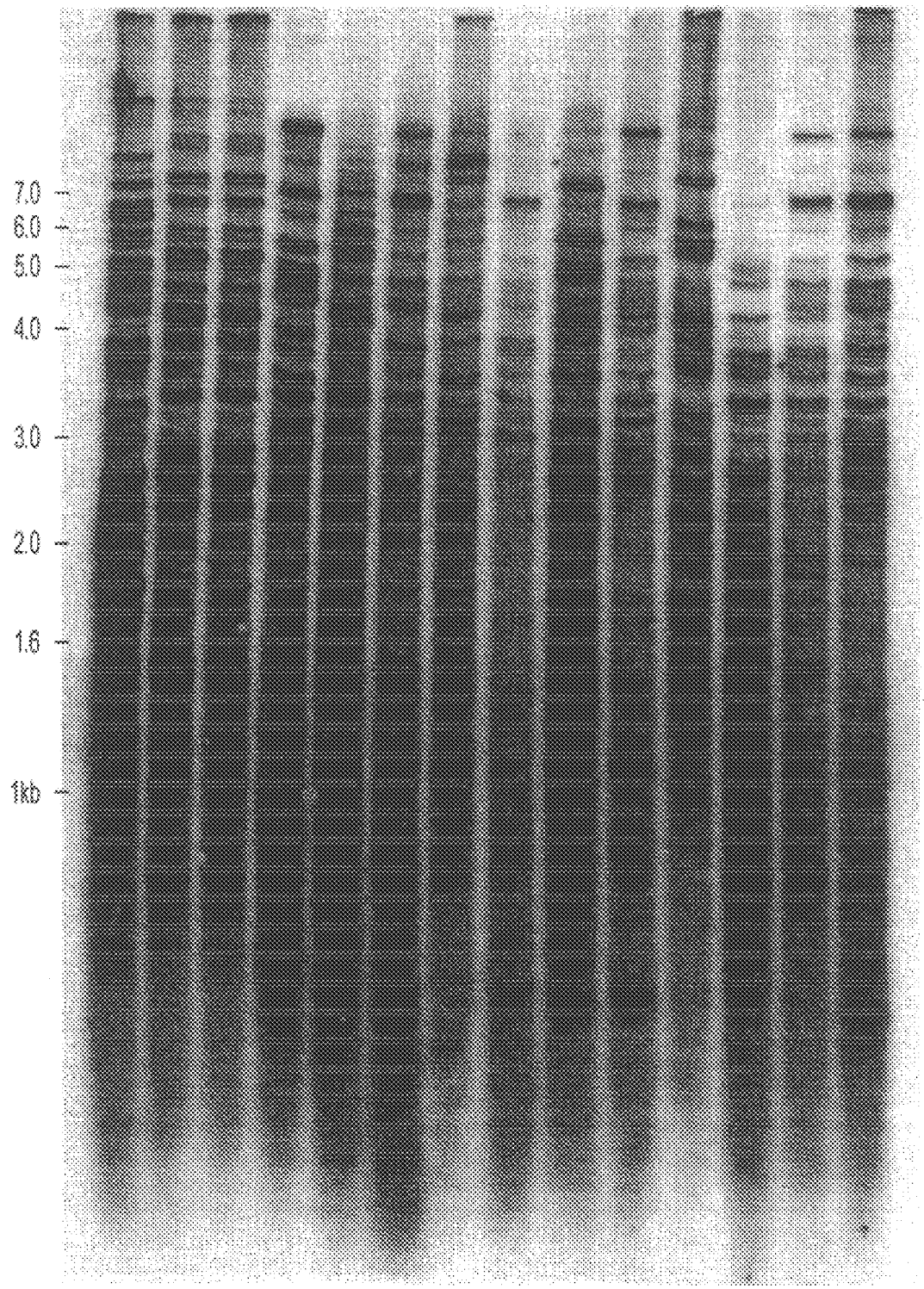
FIG. 5 is a Southern blot of DNA cut with Hinf I and probed using the multi-locus Jefferys probe (33.6) showing the distinct and identifying pattern of a number of illustrative myoepithelial cell lines and xenografts disclosed herein (HMS-1, HMS-X, HMS-3, HMS-3X, HMS-4X). All of the myoepithelial cell lines and xenografts exhibited the same susceptibility to recombinant adeno-virus associated virus transfection and the same resistance to adenoviral transfection. Other myoepithelial cell lines and xenografts (HMS-5X, HMS-6X, HMS-5, HMS-6) not depicted exhibit the same properties.
Figure 6:
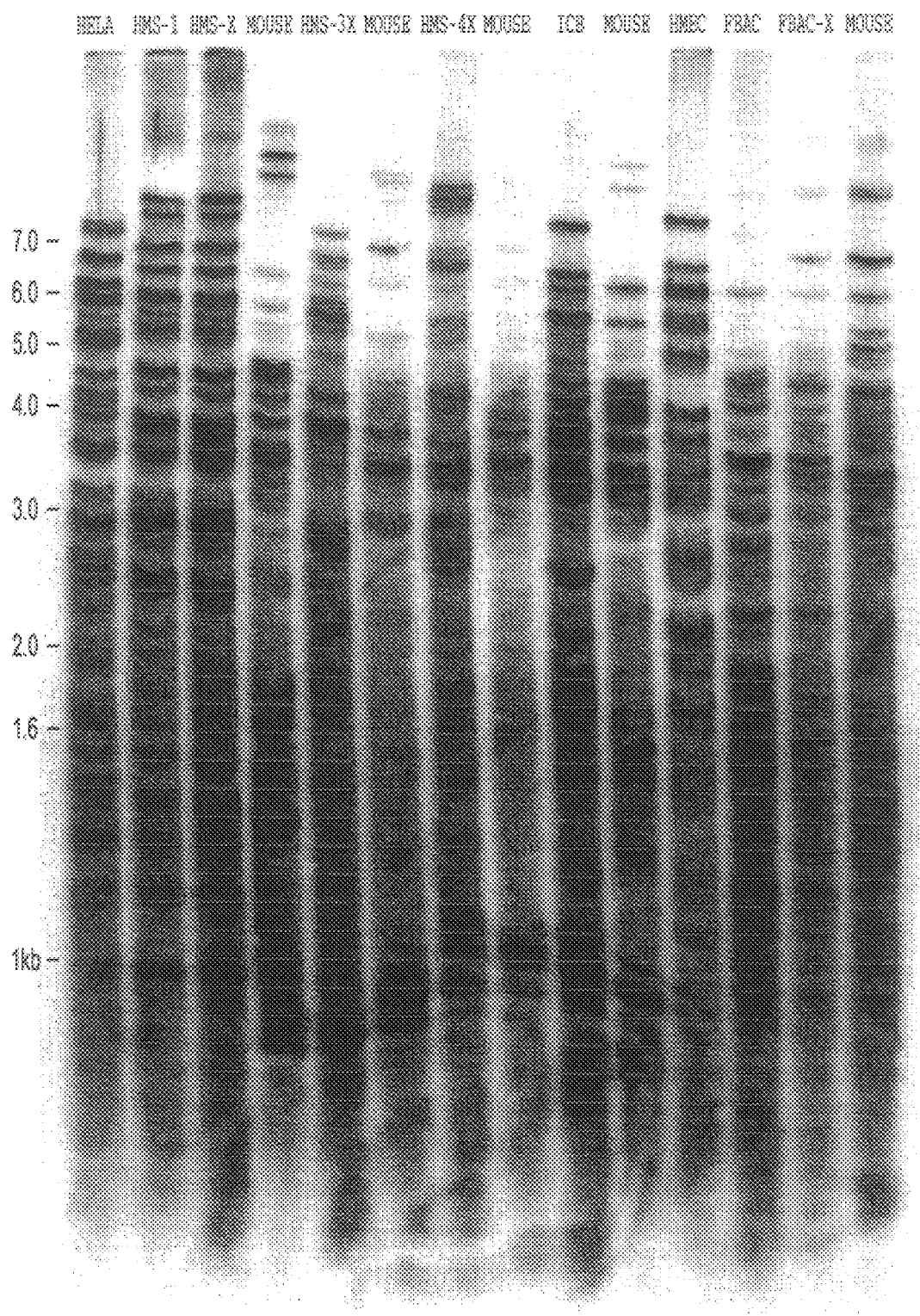
FIG. 6 is a Southern blot of DNA cut with Hae III and probed using the multi-locus Jefferys probe (33.6) showing the distinct and identifying pattern of a number of illustrative myoepithelial cell lines and xenografts disclosed herein (HMS-1, HMS-X, HMS-3, HMS-3X, HMS-4X). All of the myoepithelial cell lines and xenografts exhibited the same susceptibility to recombinant adeno-virus associated virus transfection and the same resistance to adenoviral transfection. Other myoepithelial cell lines and xenografts (HMS-5X, HMS-6X, HMS-5, HMS-6) not depicted exhibit the same properties.

As noted above, certain viral vectors may be able to gain entry in to cells through multiple receptors expressed on the surface of a cell. For example, adeno-associated virus 2 may be able to gain entry in to cells via the human fibroblast growth factor receptor 1 or αVβ integrin (see e.g. see e.g. Summerford et al., Nat. Med. 5(1): 78–82 (1999) and Qing et al., Nat. Med. 5(1): 71–11 (1999)). Therefore, it is important to establish that any vector (adeno-associated virus 2 or otherwise) used to selectively transduce myoepithelial cells will not transduce proximal epithelial cells. In particular, as certain vectors may be able to gain entry into a target cell by more than one receptor, it is prudent to assess the cellular specificity of any candidate vectors. Methods for assessing the specificity of a candidate vector are well known in the art and consist merely of contacting a target cell of interest with a candidate vector and observing if transduction occurs. In this context, FIG. 4 provides an illustrative example of an assessment of the Adeno-associated virus-2 used in the disclosed examples. In particular, FIG. 4A shows reporter gene expression in myoepithelial cells contacted with a recombinant adeno-associated virus containing a human green fluorescence reporter gene and illustrates how the expression of heparin sulfate proteoglycan on the surface of myoepithelial cells allows the selective targeting of the myoepithelial cells. In comparison, FIG. 4B shows only background reporter gene expression in epithelial cells contacted with a recombinant adeno-associated virus containing a human green fluorescence reporter gene and illustrates how the expression of heparin sulfate proteoglycan on the surface of myoepithelial cells allows the selective transduction of the myoepithelial cells.

Generation and Manipulation of Vectors of the Invention

Methods for generating and manipulating vectors such as the recombinant adeno-associated virus and adenovirus vectors disclosed herein are well known in the art, for example in U.S. Pat. Nos. 5,681,731, 5,585,362, 5,756,283 and 5,843,742 which are incorporated herein by reference. As discussed below, a variety of art accepted techniques may be utilized in the practice of embodiments of the invention disclosed herein. While the vectors of the invention may be know in the art such as replication-competent lytic adenoviruses, the vectors can also be manipulated to facilitate their use in the methods disclosed herein. For example, a nucleic acid (eg., cDNA or genomic DNA) containing a regulatory region such as a promoter or an enhancer may be inserted into a cell specific vector for cloning (amplification of the DNA) or for expression. Alternatively, a nucleic acid encoding a gene of interest such as a suicide gene or tumor suppressive gene maybe inserted into a cell specific vector for expression in a target cell.

The nucleic acid sequence of interest may be inserted into a vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

Both expression and cloning vectors can contain a nucleic acid sequence that enables the vector to replicate in one or more selected host cells. Such sequences are well known for a variety of mammalian, bacteria, yeast, and viruses. The origin of replication from the plasmid pBR322 is suitable for most Gram-negative bacteria, the 2: plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up a nucleic acid of interest, such as Neomycin, DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp[7] (Stinchcomb et al., *Nature*, 282:39 (1979); Kingsman et al., *Gene*, 7:141 (1979); Tschemper et al., *Gene*, 10:157 (1980)). The trp1 gene provides a selection marker for a mutant strain of yeast lacking the ability to grow in tryptophan, for example, ATCC No. 44076 or PEP4-1 (Jones, *Genetics*, 85:12 (1977)).

Expression and cloning vectors can contain a promoter operably linked to the nucleic acid sequence to direct mRNA synthesis. Promoters recognized by a variety of potential host cells are well known. Promoters suitable for use with prokaryotic hosts include the β-lactamase and lactose promoter systems (Chang et al., *Nature*, 275:615 (1978); Goeddel et al., *Nature*, 281:544 (1979)), alkaline phosphatase, a tryptophan (trp) promoter system (Goeddel, *Nucleic Acids Res.*, 8:4057 (1980); EP 36,776), and hybrid promoters such as the tac promoter (deBoer et al., *Proc. Natl. Acad. Sci. USA*, 80.21–25 (1983)). Promoters for use in bacterial systems also will contain a Shine-Dalgarno (S.D.) sequence operably linked to the DNA encoding a nucleic acid of interest.

Transcription from vectors in mammalian host cells can be controlled, for example, by promoters obtained from the genomes of viruses such as polyoma virus, fowlpox virus (UK 2,211,504 published Jul. 5, 1989), adenovirus (such as Adenovirus 2), bovine papilioma virus, avian sarcoma virus, cytomegalovirus, a retrovirus, hepatitis-B virus and Simian Virus 40 (SV40), from heterologous mammalin promoters, e.g., the actin promoter or an immunoglobulin promoter, and from heat-shock promoters, provided such promoters are compatible with the host cell systems. In addition, a polynucleotide of interest can be under the transcriptional regulation of an inducible promoter such as the Tet promoter. Alternatively, it can be under the control of an epithelial tissue-specific or cell-specific promoter. Epithelial cell-specific promoters, such as whey acidic protein (wap), can be used to target expression of a given gene, e.g., a suicide gene, in ductal epithelial cells. Use can also be made of promoters which control wild-type tumor suppressor genes, such as Maspin, p53 or Mcs-1 (rat), homeobox genes which are expressed in normal cells but not in cancerous cells.

Transcription of a DNA encoding a polynucleotide of interest by mammalian cells may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, "-fetoprotein, and insulin). Typically, however, one will use an enhancer from a eucaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the coding sequence, but is preferably located at a site 5' from the promoter.

Methods for Selectively Transducing Epithelial and Myoepithelial Cells

The methods of the invention disclosed herein allow the selective transduction of both ductal epithelial and myoepithelial cells. An illustrative embodiment of the invention is a method of selectively transducing a cell within a mixed population of ductal epithelial and myoepithelial cells, comprising the step of contacting the cell with a cell specific vector that transduces the cell through a molecule that is expressed only on the ductal epithelial cell or, alternatively, through a different molecule that is expressed only on the myoepithelial cell. In a preferred embodiment of this invention, the mixed population of ductal epithelial and myoepithelial cells is within a ductal system of a mammary gland and the cells to be transduced are contacted with the vector by ductal cannulation.

In a specific embodiment of this invention, cell is a ductal epithelial cell that is transduced with a vector (such as a replication competent adenovirus) that induces cell death. In a related embodiment, the vector can contain a suicide gene that can induce cell death such as thymidine liase or cytosine deaminase. In another specific embodiment of the invention, the vector contains a as element which stimulates viral replication or specific gene expression in the presence of a trans factor present in the ductal epithelial cell. For example, the cis element could be one of the large number of known regulatory sequences such as the lactoalbumin promoter and the MUCI promoter.

In yet another preferred embodiment of this invention, the cell is a myoepithelial cell that is transduced with a vector (such as a recombinant adeno-associated virus) that comprises a gene encoding a polypeptide which inhibits the development of cancer. In a specific embodiment of this invention, the vector contains a cis element contains a cis element which modulates the expression of the gene in the presence of a trans factor present in the myoepithelial cell. In preferred embodiments of this method, the polypeptide inhibits the proliferation of a ductal epithelial cell, the invasion of a ductal epithelial cell, endothelial migration, angiogenesis or increases the production of nitric oxide by the myoepithelial cell. Illustrative polypeptides include maspin, thrombospondin-1, TIMP-1, protease nexin-II, $\alpha$-1 antitrypsin and soluble bFGF receptor. Preferably the polypeptide induces death (for example by apoptosis) of a ductal epithelial cell.

In a related embodiment, the invention consists of a method of selectively transducing a cell in a ductal system in a mammary gland selected from the group consisting of a ductal epithelial cell and a myoepithelial cell, comprising the step of contacting, by ductal cannulation, the cell with a vector that selectively targets a CAR molecule that is expressed on the ductal epithelial cell or a heparin sulfate proteoglycan molecule that is expressed on the myoepithelial cell. In yet another related embodiment, the invention consists of a method of selectively transducing a ductal epithelial cell in a ductal system in a mammary gland, comprising the step of contacting, by ductal cannulation, the cell with a vector that targets a CAR molecule expressed by the cell. In yet another related embodiment, the invention consists of a method of selectively transducing a myoepithelial cell in a ductal system in a mammary gland, comprising the step of contacting, by ductal cannulation, the cell with a vector that targets a heparin sulfate proteoglycan molecule expressed by the cell.

In a related embodiment, the invention is a method of transducing ductal epithelial cells within a mixed population of ductal epithelial and myoepithelial cells, while not transducing proximal myoepithelial cells, by contacting the ductal epithelial cells with a vector that gains entry into ductal epithelial cells via a CAR molecule expressed by the ductal epithelial cells. In yet another related embodiment, the invention consists of a method of transducing ductal epithelial cells within a mixed population of ductal epithelial and myoepithelial cells, wherein the myoepithelial cells are not transduced, by contacting the ductal epithelial cells with a vector that gains entry into the ductal epithelial cells via a CAR molecule expressed by the ductal epithelial cells but not expressed by the myoepithelial cells.

In yet another related embodiment, the invention consists of a method of transducing myoepithelial cells within a mixed population of ductal epithelial and myoepithelial cells, while not transducing proximal ductal epithelial cells, by contacting the myoepithelial cells with a vector that gains entry into myoepithelial cells via a heparin sulfate proteoglycan molecule expressed by the myoepithelial cells. In yet another related embodiment, the invention consists of a method of transducing myoepithelial cells within a mixed population of ductal epithelial and myoepithelial cells, wherein the ductal epithelial cells are not transduced, by contacting the myoepithelial cells with a vector that gains entry into the myoepithelial cells via a heparin sulfate proteoglycan molecule expressed by the myoepithelial cells but not expressed by the ductal epithelial cells.

Prophylactic Methods for Treating a Breast Duct

The prophylactic methods of the present invention involve methods of selectively treating a cell in the duct of a breast prophylactically for a disease that affects the ductal epithelium of the breast such as cancer. One embodiment of these methods consists of selectively transducing either a luminal epithellal cell, a myoepithelial cell (or both a luminal epithelial cell and a myoepithelial cell) within the duct of a breast, by using ductal cannulation to contacting the cell of interest with a vector that selectively targets a molecule that is expressed on either the luminal epithelial cell or the myoepithelial cell. Depending upon which cell is contacted, the vectors used in these methods are then used to effect a desired biological activity such as cytolysis or the expression of a soluble effector molecule.

In an exemplary embodiment, the method comprises contacting, preferably by ductal cannulation, a myoepithelial or epithelial cell with a cell specific vector that either suppresses the growth of cancerous cells or effects the destruction of all or less than all of the ductal epithelium so as to inhibit the formation of cancer of ductal epithelial origin. In another illustrative embodiment, the invention consists of a method of treating the ductal epithelium of a mammary gland for cancer of ductal epithelial cell origin, comprising the step of contacting, by ductal cannulation, a cell in a ductal system in a mammary gland selected from the group consisting of a ductal epithelial cell and a myoepithelial cell, with a vector that enters the cell through a CAR molecule expressed by the ductal epithelial cell or a heparin sulfate proteoglycan molecule expressed by the myoepithelial cell, wherein the expression of the polynucleotides of the vector so transduced inhibits the formation of cancer of ductal epithelial cell origin.

In a specific embodiment of the prophylactic methods of the present invention, epithelial cells of the mammary gland are treated prophylactically with a cytotoxic cell specific vector so as to inhibit the formation of cancer of ductal epithelial origin. In this context, only those cytolytic viruses which exhibit the proper cell specificity (i.e. those which selectively transduce epithelial cells via the CAR molecule expressed by these cells) can be used in the methods of the invention. In another specific embodiment of the prophylactic methods of the present invention, myoepithelial cells of the mammary gland are treated prophylactically with a cell specific vector comprising a polynucleotide encoding a suppressor molecule so as to inhibit the formation of cancer of ductal epithelial origin.

The prophylactic methods of treating a mammary gland described herein are particularly useful in treating a mammary gland in a mammal at risk for developing breast cancer. The mammary gland can be characterized as one that has never had a tumor, one that had a tumor previously but the tumor is no longer detectable due to other prior therapeutic treatment, or one that has an incipient or occult tumor, preneoplasia or ductal hyperplasia. Normally, hyperplasias and incipient and occult tumors are not detectable by means of physical examination or radiology. Accordingly, the prophylactic method will find use in cases where there is reason to take some prophylactic measures, such as when there are known inherited factors predisposing to cancers, where there are suspicious lesions present in a breast with the potential for developing into a malignancy, where there has been exposure to carcinogenic agents in the environment, where age predisposes to a cancer, where cancer of another gland, e.g., the mammary gland of the contralateral breast, suggests a propensity for developing cancer, or where there is a fear or suspicion of metastasis.

The methods of the present invention can also be combined with other methods of prophylactic and therapeutic treatment in addition to those cited herein, such as methods that target destruction of cancer cells, e.g., by targeting of cell-surface markers, receptor ligands, e.g., ligands to gastrin-releasing peptide-like receptors, tumor-associated antigens, e.g., the 57 kD cytokeratin or the antigen recognized by the monoclonal antibody GB24, the extracellular matrix glycoprotein tenascin, antisense oncogenes such as c-fos, homeobox genes that are expressed in cancer cells but not normal cells, tumor-infiltrating lymphocytes that express cytokines, RGD-containing peptides and proteins, which are administered following surgery, lipophilic drug-containing liposomes to which are covalently conjugated monoclonal antibodies for targeting to cancer cells, low fat diet, moderate physical exercise and hormonal modulation.

Introduction of Vectors via Ductal Cannulation

The ductal epithelium is preferably contacted with the agent by introduction of the agent through the duct of the exocrine ductal epithelium, such as by ductal cannulation. In the mammary gland, there are 6–9 major ducts that emanate from the nipple and serially branch into other ducts, terminating in lobulo-alveolar structures (Russo et al. (1990), supra). Accordingly, in some circumstances, such as those in which even more localized treatment is necessary or desired, for example, by the choice of anti-cancer agent, it may be preferable to contact the ductal epithelium of the exocrine gland through one of these major ducts connecting to a lobulo-alveolar structure. In this regard, ductal cannulation enables intratumoral injection.

Methods of ductal cannulation are known in the art (see e.g. S. M. Love and S. H. Barsky (1996) The Lancet, 348:997–999; Makita et al., Breast Cancer Res. Treat. 18: 179–188 (1991) and Okazaki et al., Jpn J Clin Oncol 21: 188–193 (1991)). Briefly, a breast can prepared and draped, with the breast-duct orifices identified with magnifying loupes or the methods described below. One or more ducts can then be cannulated with cannula known in the art such as a rigid metal duct-probe (6 FR Taber-Rothschild Galactrography Kit, Manan Medical Products Inc., Northbrook, Ill.).

In order to facilitate the location individual orifices in a nipple of a breast, one can employ methods for transiently marking and locating individual orifices in a nipple of a breast as further described in U.S. Ser. No. 09/153,564, incorporated herein by reference. Moreover, methods for gaining access and evaluating cells of a breast duct as further described in U.S. Ser. Nos. 09/067,661 and 09/301,058, incorporated herein by reference. For example, one can introduce a detectable substance, such as a labeling reagent, dye, or the like, to the nipple so that the substance localizes and/or accumulates at or near the orifice to permit visual, automated, or other detection. Alternatively, one can utilize other stimuli for inducing a response, change, or reaction at or near a location of the orifice in the nipple. For example, it may be possible to illuminate the nipple with certain light or other energies which help distinguish between the orifice and other tissue surfaces. It may also be possible to introduce chemical reagents which react with ductal secretions at the orifice to enhance visibility e.g. to produce a visible or otherwise detectable reaction product.

Methods Targeting Epithelial Cells

In a specific embodiment of the prophylactic methods of the present invention, luminal epithelial cells in a mammary gland are treated prophylactically for cancer so as to inhibit the formation of cancer of ductal epithelial origin. The method comprises contacting, preferably by ductal cannulation, a luminal epithelial cell in the mammary gland with a vector that selectively targets the luminal epithelial cell. In a preferred embodiment, the vector is a replication competent adenovirus which targets a CAR molecule expressed by the luminal epithelial cell and subsequently induces cell death by lysis. In another embodiment, the vector contains a suicide gene such as thymidine kinase or cytosine deaminase and induces cell death via apoptosis. In a more preferred embodiment, the replication-competent lytic adenovirus contains a cis element such as a lactoalbumin promoter and the MUCI promoter which stimulates adenovirus replication in the presence of a trans factor present in the epithelial cell which enhances viral replication, lysis and cell death. With respect to the replication competent adenovirus strategy, the resistance of myoepithelial cells to adenovirus infection inhibits systemic infection by adenovirus and limits the gene and/or viral therapy to the ductal system of the breast.

Other vectors are contemplated in addition the adenovirus viral vectors described herein. For example, coxsackie viruses also target cells through the CAR molecule (see e.g. Bergelson et al., Science 275(5304): 1320–1323 (1997). Therefore, coxsackie virus vectors can also be used to selectively transduce a cell in a ductal system in a mammary gland that expresses CAR molecules. Moreover, it is known in the art that a wide variety of vectors may be constructed to target a specific molecule, such as CAR, on a cell. In particular, target cell specificity of delivery vectors can be provided by incorporation of a target cell specific binding domain by the use of any binding domain, which binds specifically to a binding site on the target cell (see e.g. U.S. Pat. No. 5,834,589).

As discussed above, a cell specific vector such as the adenoviral vectors disclosed herein can further comprise a suicide gene to enhance the destruction of epithelial cells in the breast. For example, a vector comprising a suicide gene, upon transformation of a epithelial cell and expression therein, renders the transformed cell sensitive to the epithelium-destroying agent, increases the sensitivity of the transformed cell to the agent, converts the agent from a prodrug to an active drug, activates the conversion of the agent from a prodrug to an active drug, enhances the effect of the agent or, itself, produces a protein that is cytotoxic. A preferred suicide gene for use in the present inventive methods is thymidine kinase, such as is found in the Herpes simplex virus, which phosphorylates nucleoside analogues including gancyclovir, which, in turn, inhibits DNA replication. Another example of a suicide gene is cytosine deaminase, which is used in conjunction with 5-fluorocycosine. If the vector comprising the suicide gene is administered locally to the ducts, the cytotoxic agent or precursor can be administered systemically, since only transfected cells will be affected. In this regard, the bystander effect, i.e., the death of neighboring uninfected cells, presumably due to transfer of toxic byproducts through gap junctions between cells in the same compartment, obviates the need for every cell in the ductal epithelium, which is to be destroyed, to be infected. However, sufficient time must be allowed between contacting the epithelial cell with the suicide gene and the prodrug, for example, to achieve efficient killing of the breast epithelial cells.

A cell specific vector comprising an apoptosis-inducing gene also can be used as an agent that destroys a epithelial cell of a breast (Vaux, Cell 76:777–779 (1994)). Examples of apoptosis-inducing genes include ced genes, myc genes (overexpressed), the bclxs gene, the bax gene, and the bak gene. The apoptosis-inducing gene causes death of transfected cells, i.e., by inducing programmed cell death. For example, the bclxs gene, bax gene, or bak gene can be used to inhibit bcl-2 or bcl-X(L), leading to apoptosis. Where necessary, a vector comprising an apoptosis-inducing gene can be used in combination with an agent that inactivates apoptosis inhibitors such as bcl-z, p35, IAP, NAIP, DAD1 and A20 proteins.

Suicide and apoptosis genes can be administered by way of a cell specific vector, such as the adenoviral vectors described in the Examples below. Adenoviral vectors are favored because they enable the generation of high titer recombinant viruses and the efficient transduction of post-mitotic cells because adenoviral DNA exists as an episome in the nucleus (Verma, Molecular Medicine 1:2–3 (1994)).

Methods Targeting Myoepithehal Cells

In another embodiment of the prophylactic methods of the present invention, the myoepithelium of a mammary gland can be treated prophylactically for cancer so as to inhibit the formation of cancer of ductal epithelial origin. The method comprises contacting, preferably by ductal cannulation, the myoepithelium of the mammary gland with a vector comprising a molecule which can inhibit the formation of cancer of ductal epithelial origin, for example, maspin. In a preferred embodiment, the vector is a recombinant adeno-associated virus which targets a heparin sulfate proteoglycan molecule expressed by the myoepithelial cell and comprises a polypeptide which inhibits the development of epithelial cell cancer. In a specific embodiment, the polypeptide of the recombinant adeno-associated virus inhibits angiogenesis or the proliferation, invasion or metastases of a luminal epithelial cell. In a specific embodiment, the polypeptide is maspin, thrombospondin-1, TIMP-1, protease nexin-II, α-1 antitrypsin or soluble bFGF receptor.

Other vectors are contemplated in addition the adeno-associated viral vectors described herein. For example, herpesviruses are believed to target cells through their heparin sulfate proteoglycan molecules (see e.g. Zhu et al., P.N.A.S. 92(8): 3546–3550 (1995)). Therefore, herpesvirus vectors such as those known in the art (see e.g. Levatte et al., Neuroscience 86(4): 1321–1336 (1998)), can also be used to selectively transduce a cell in a ductal system in a mammary gland that expresses heparin sulfate proteoglycan molecules. Moreover, it is known in the art that a wide variety of vectors may be constructed to target a specific molecule, such as heparin sulfate proteoglycan, on a cell. In particular, target cell specificity of delivery vectors can be provided by incorporation of a target cell specific binding domain by the use of any binding domain, which binds specifically to a binding site on the target cell (see e.g. U.S. Pat. No. 5,834,589).

Therapeutic Methods for Treating a Breast Duct

Embodiments of therapeutic methods of the present invention are related to and can parallel the prophylactic methods described above and include treating the ductal epithelium of a breast therapeutically for a disease that affects the ductal epithelium In one embodiment of the therapeutic methods of the present invention, the ductal epithelium of a mammary gland is treated therapeutically for cancer so as to destroy cancerous and noncancerous epithelial cells of the ductal epithelium and inhibit the spread of cancer. In an exemplary embodiment, the method comprises contacting, preferably by ductal cannulation, a myoepithelial or epithelial cell with a cell specific vector that can either effect the suppression of the growth of cancerous cells or effect the destruction of all or less than all cancerous cells of ductal epithelial origin. In a specific embodiment of the therapeutic methods of the present invention, epithelial cells of the mammary gland are contacted with a cytotoxic cell specific vector so as to destroy cancerous cells of ductal epithelial origin. In another specific embodiment of the therapeutic methods of the present invention, myoepithelial cells of the gland are contacted with a cell specific vector comprising a polynucleotide encoding suppressor molecule so as to inhibit the progression of cancers of ductal epithelial origin. In such therapeutic methods, the epithelial-destroying agent should suppress the growth of or destroy all of the diseased or malignant epithelium. In addition, the ductal epithelium immediately surrounding the diseased/malignant epithelium also preferably should be suppressed or destroyed.

Combined Therapeutic/Prophylactic Methods for Treating a Breast Duct

The present invention also provides methods of treating the ductal epithelium of a mammary gland using prophylactic and therapeutic methods known in the art in combination with the prophylactic and therapeutic methods disclosed herein. Examples of such art accepted methods include surgical removal of the cancerous tissue, radiation therapy and chemotherapy. Such combination methods would then comprise an art accepted methods such as the surgical removal of the cancerous tissue and then further contacting, either concomitantly with or subsequently to the therapeutic treatment, the ductal epithelium of the mammary gland, e.g., by ductal cannulation, with the cell specific vectors disclosed herein, so as to suppress or destroy any remaining cancerous cells and noncancerous cells and to inhibit the spread of cancer.

Diagnostic Methods for Evaluating a Breast Duct for Cancer

The present invention further allows for the utilization of cell specific vectors containing reporter genes in diagnostic studies which can evaluate the expansion of a specific cell lineage. Specifically, using the selective transduction methods described herein, one can determine whether a group of cells (such as proliferating cells) within the duct of a breast belongs to either the epithelial or myoepithelial lineages. For example one can use ductal cannulation to expose luminal epithelial cells with a cell specific vector (such as replication-defective rAd) containing a reporter gene in order to evaluate the expansion of this cancer associated lineage. Alternatively, one can use ductal cannulation to expose myoepithelial cells with a cell specific vector (such as rAAV) containing a reporter gene in order to evaluate the expansion of this lineage. In this way a practitioner can determine whether a group of cells (such as a group of proliferating cells) is, like luminal epithelial cells, prone to cancer. In addition, methods utilizing cell specific vectors containing reporter genes can be used to facilitate the assessment of the presence of occult cancer cells, thereby aiding in long term prognosis and treatment.

In a preferred embodiment of the invention, the method consists of determining the lineage of a cell in a ductal system in a mammary gland selected from the group consisting of a luminal epithelial cell and a myoepithelial cell, by using ductal cannulation to contact the cell with vector containing a reporter gene, wherein the vector selectively targets a molecule that is expressed on the luminal epithelial cell or the myoepithelial cell. As shown for example in FIGS. 3 and 4, the expression of the reporter gene can be used as an indication of transduction of the cell with the specificity of the vector providing the information as to the cell lineage.

A wide variety of reporter genes and assays that are known in the art can be adapted to the diagnostic methods disclosed herein. For example, a reporter gene can encode an enzyme which produces colorimetric or fluorometric change in the host cell which is detectable by in situ analysis and which is a quantitative or semi-quantitative function of transcriptional activation. Exemplary enzymes include esterases, phosphatases, proteases (tissue plasminogen activator or urokinase) and other enzymes capable of being detected by activity which generates a chromophore or fluorophore as will be known to those skilled in the art. A preferred example is $E. coli$ beta-galactosidase disclosed herein. This enzyme produces a color change upon cleavage of the indigogenic substrate indolyl-B-D-galactoside by cells bearing beta-galactosidase (see, e.g., Goring et al., Science, 235:456–458 (1987) and Price et al., Proc. Natl. Acad. Sci. U.S.A., 84:156–160 (1987)). This enzyme is preferred because the endogenous β-galactosidase activity in mammalian cells ordinarily is quite low, the analytic screening system using β-galactosidase is not hampered by host cell background.

Compositions of the Invention

In order to facilitate the utilization of vectors useful in gene therapy targeting cells of the breast duct, immortalized myoepithelial cell lines and transplantable xenografts were established from benign human myoepitheliomas of the salivary gland (HMS-1, HMS-X; HMS-3, HMS-3X), breast (HMS-4, HMS-4X) and bronchus (HMS-6, HMS-6X) (M. D. Sternlicht et al. (1996) In Vitro, 32:550563; M. D. Sternlicht et al. (1997) Clin. Cancer Res., 3:1949–1958; Z. Shao et al. (1998) Exper. Cell Res., 241:394–403). These cell lines and xenografts express identical myoepithelial markers as their in situ counterparts and display an essentially normal diploid karyotype. The myoepithelial cell lines and xenografts and myoepithelial cells in situ constitutively express high amounts of proteinase and angiogenesis inhibitors which include TIMP-1, protease nexin-II, I-1 antitrypsin, thrombospondin-1, soluble bFGF receptors, and maspin. These suppressor molecules are well known in the art. (See generally, Sternlict et al., Lab. Invest. 74(4) :781–796 (1996) and Sternlict et al., Med. Hypo. 48:37–46 (1997). In addition, for TIMP-1, see U.S. Pat. No. 5,595,885, for protease nexin-II, see U.S. Pat. No. 5,213,962, for α-1 antitrypsin see U.S. Pat. No. 5,736,379, for thrombospondin-1 see U.S. Pat. No. 5,648,461, for bFGF receptors see 5,750,371, and for maspin see U.S. Pat. No. 5,470,970.

The human myoepithelial cell lines inhibit both ER-positive and ER-negative breast carcinoma cell invasion and endothelial migration and proliferation (angiogenesis) in vitro. The myoepithelial cell lines also inhibit breast carcinoma proliferation through an induction of breast carcinoma cell apoptosis, a phenomenon which occurs at high levels within DCIS (Z. Shao et al. (1998) Exper. Cell Res., 241:394–403). On the basis of immunoprecipitation studies, myoepithelial maspin seems to be the major effector molecule which inhibits invasion and thrombospondin-1 seems to be the major effector molecule which inhibits angiogenesis (S. Bodis et al. (1996) Cancer, 77:1831–1835). Myoepithelial nitric oxide seems to the major effector molecule which inhibits breast carcinoma proliferation through its induction of apoptosis (Z. Shao et al. (1998) Multidiscip. Symposium on Breast Disease).

The present invention is further detailed in the following Examples, which are offered by way of illustration and are not intended to limit the invention in any manner. All patent and literature references cited in the present specification are hereby incorporated by reference in their entirety.

EXAMPLES

Example 1

Treansections of Cells whit Adenovirus

This example relates to the finding is that primary breast ductal epithelial cells express CAR and are easily transduced with rAd whereas myoepithelial cells lack CAR and are completely resistant. CAR is thought to mediate, in part, the attachment of adenovirus to the cell membrane (J. Bergelson et al. (1997) Science 275:1320–1323). In this context, one can use the rAd studies described below as an illustration of methods of the present invention.

rAd Studies: One can use a replication-defective rAd2 (see e.g. Hashimoto et al., Biochem. Biophys. Res. Comm., 240: 88–92 (1997)) with a β-galactosidase reporter and measure its ability to transduce epithelial cells compared to myoepithelial cells through ex vivo and in vivo approaches. In addition, one can use mastectomy specimens and deliver the rAd intraductally as was done with rAAV in Example 2 below. Because rAd does not does not integrate (unlike rAVV), the incubation period will probably be less (on the order of 72–96 hours). One can detect β-galactosidase by a substrate assay in frozen sections of the mastectomy specimens. One can then compare myoepithelial to epithelial colorimetric development. In parallel experiments one can deliver intraductally rAd to anesthetized rabbits and after a few days observe β-galactosidase activity in their breast sections. At this point, one can compare epithelial activity with myoepithelial activity. Even in situations using a replication-defective virus one can nevertheless measure adenovirus titers in the feces and urine of the rabbits by ELISA to evaluate how the myoepithelial layer offers a barrier to systemic infection.

Example 2

Transfection of Cells with Adeno-associated Virus

This example relates to the finding that unlike epithelial cells expression of CAR, myoepithelial cells, instead, express cell surface heparin sulfate proteoglycan (HS) and are easily transduced with rAAV. As discussed in Example 1 above, primary ductal epithelial cells have absence of this proteoglycan and are resistant to rAAV. Cell surface HS is thought to be a receptor for rAAV which determines transducibility (C. Summerford and R. J. Samulski, J. Virology 72:1438–1445). In this context, one can use the rAAV studies described below as an illustration of methods of the present invention. Up until we established that rAAV can be used to successfully transfect myoepithelial cells (HMS-1), our myoepithelial cell lines were completely resistant to transfection by all conventional means.

rAAV Studies: One can begin with rAAV (see e.g. Flannery et al., P.N.A.S., 94: 6916–6921, (1997)). This recombinant virus contains a CMV promoter and the human green fluorescent protein. One can then inject increasing titers of this virus together with a supravital dye, e.g. lymphazurin (the sentinel node dye) to help guide the injections into the tumor's center. One can then inject the myoepithelial xenografts disclosed herein (HMS-X, HMS-3X, HMS-4X, HMS-6X) of a size of 1 cm in diameter and after 1–3 weeks extirpate these tumors, cut thin frozen sections and study the radial distribution of fluorescence in relation to the azure blue dye. As controls, one can use non-myoepithelial carcinoma tumors where one would expect transduction to be absent or minimal. One can then determine how rAAV transduction into myoepithelial cells followed by recombinant gene expression occurs in vivo by these direct tumoral injection studies. If positive results are obtained one can deliver rAAV intraductally via nipple cannulation into human mastectomy specimens ex vivo and into rabbit nipples in vivo. After 24 hours one can initiate organ culture explants of the mastectomies and then after several weeks observe fluorescence in myoepithelial cells compared to ductal epithelial cell. Since rabbits have eight nipples with 4 ductal systems each they provide a relatively simple animal model to test intraductal gene delivery. After three weeks one can sacrifice the rabbits, section their breasts and compare myoepithelial to epithelial fluorescence.

Example 3
Verifying Observations Concerning Cell-specific Targeting of Recombinant Adenovirus (rAd) and Recombinant Adeno-associated Virus (rAAV) on Epithelial and Myoepithelial Cells Respectively Using in vitro experiments, we expand upon our earlier findings and outline the parameters that will facilitate in vivo practice of the invention. These parameters include determinations of dose (titer), frequency of administration, period of incubation, period of observation, etc. Controls for all of these correlative in vitro experiments include both non-reporter vector or no vector.

In addition, we rule out the possibility of a pseudotransduction phenomenon occurring in these examples (vector-mediated protein delivery rather than gene expression) especially in the rAAV experiments where this phenomenon has been observed by others. For example, in experiments where successful reporter gene product is observed, we verify that it is gene expression that we are delivering rather than just protein by carrying out a titer dilution experiment. Specifically, the effects of titer dilution should be to decrease protein staining in all cells if we are dealing with pseudotransfection; in true transfection there should be a decrease in the number of cells showing marker protein but the intensity of staining in the positive cells should not decrease. Our results establish that we are dealing with true transfection since we have made the latter observations. Furthermore in our in vitro rAAV experiments performed to date, the intensity of the reporter staining to human green fluorescent protein in the transfected HMS-1 cells increased at 3 weeks verus 1 week after transfection. This increase in reporter protein with increasing passage is indicative of true gene expression because rAAV delivered genes are always a bit slow to show full expression. If we were experiencing pseudotransfection (vector-mediated protein delivery, the reporter staining would decrease with passage.

In addition, we have backed up our proposed marker gene expression assays with a molecular genetic analysis showing the presence of virus by PCR studies.

Expanding upon our initial studies we conducted kinetic studies of transduction efficiency of reporter genes via their respective viral vectors into epithelial and myoepithelial cells in vitro.

In addition, we confirm the usefulness of E1A-deleted rAd containing two different promoters known in the art, i.e., CMV and RSV LTR.

Dose-response studies designed to determine whether there is a relationship between the vector multiplicity of infection (moi) and the efficiency of reporter gene ($\beta$-galactosidase) gene transfer into breast epithelial cells (HMEC) are included herein. Specifically, we observe that a moi of $10^2$ will achieve 100% transduction efficiency. At the same time we monitored myoepithelial cells for resistance to rAd transduction and determined that their resistance is absolute. For example, they are completely resistant to transfection even with a moi of $10^4$.

We also conducted a time course of exposure to rAd over 1–10 hours to determine whether transfection efficiency is enhanced with a longer time of exposure. It is not.

In the case of rAd, we monitored reporter gene expression over time following infection to determine its rate of expression and its decay. We find a half life of expression of 48 hours. We repeated these in vitro studies with rAAV targeting myoepithelial cells. Since rAAV as opposed to rAd integrates into the genome but requires second strand synthesis during cell division before expression occurs (since rAAV is single stranded), we would expect a longer time course after transfection to observe expression but a shallower or no rate of decay. In this context, observe that maximal expression occurs at 3 weeks with negligible decay.

We also compare reporter expression in myoepithelial cells verus epithelial cells. We evaluate replication-competent and replication-enhanced viruses whose production of viral particles can be enhanced by promoter cis/trans interactions and monitor the lysis of epithelial cells and resistance to lysis of myoepithelial cells. Significant lysis is observed visually or by a dye exclusion method (trypan blue) or by a viability monitoring method like MTT. Similar kinetic experiments have been performed. In the case of the replication-enhanced rAd, exogenous agents such as dexamethasone and/or LPS designed to increase transcription from the enhancer/promoter being used (MUC1 and lactoalbumin) in our rAd-transfected breast epithelial cells (HMEC) have been monitored for effects on viral titer and a 10 fold increase has been observed with a 50% increase in cell lysis. Myoepithelial cells remain completely resistant to the effects of this replication-competent lytic virus.

Example 4
Verifying the Feasibility of Transfecting Suppressor Molecules Such as Maspin We expand upon our in vitro experiments discussed above by using replication-defective rAd and rAAV that contain not reporter genes but native genes such as maspin and conduct similar kinetic studies. Specifically, we repeated all of the above studies that used reporter genes and instead used actual endogenous suppressor genes like maspin to establish that our approach is physiologically feasible.
Maspin Transfection into Mypepithelial Cells via rAAV Vectors The mechanisms of maspin's effects on invasion and motility inhibition are completely unknown. Maspin was initially identified by subtractive hybridization and the differential display method to identify candidate tumor suppressor genes that were defective in human breast carcinoma cells. It is interesting that even in those normal breast cell lines which were used to clone maspin and in those normal breast lines where it has been identified it is present only intracellularly and is not secreted. In contrast to epithelial cells, our myoepithelial cell lines do secrete maspin. The presence of secreted maspin in myoepithelial cells compared to normal epithelial cells and our results on maspin's invasion and motility inhibition of breast carcinoma cells support the hypothesis that maspin is acting as a paracrine and not an autocrine tumor suppressor.

Figure 7:
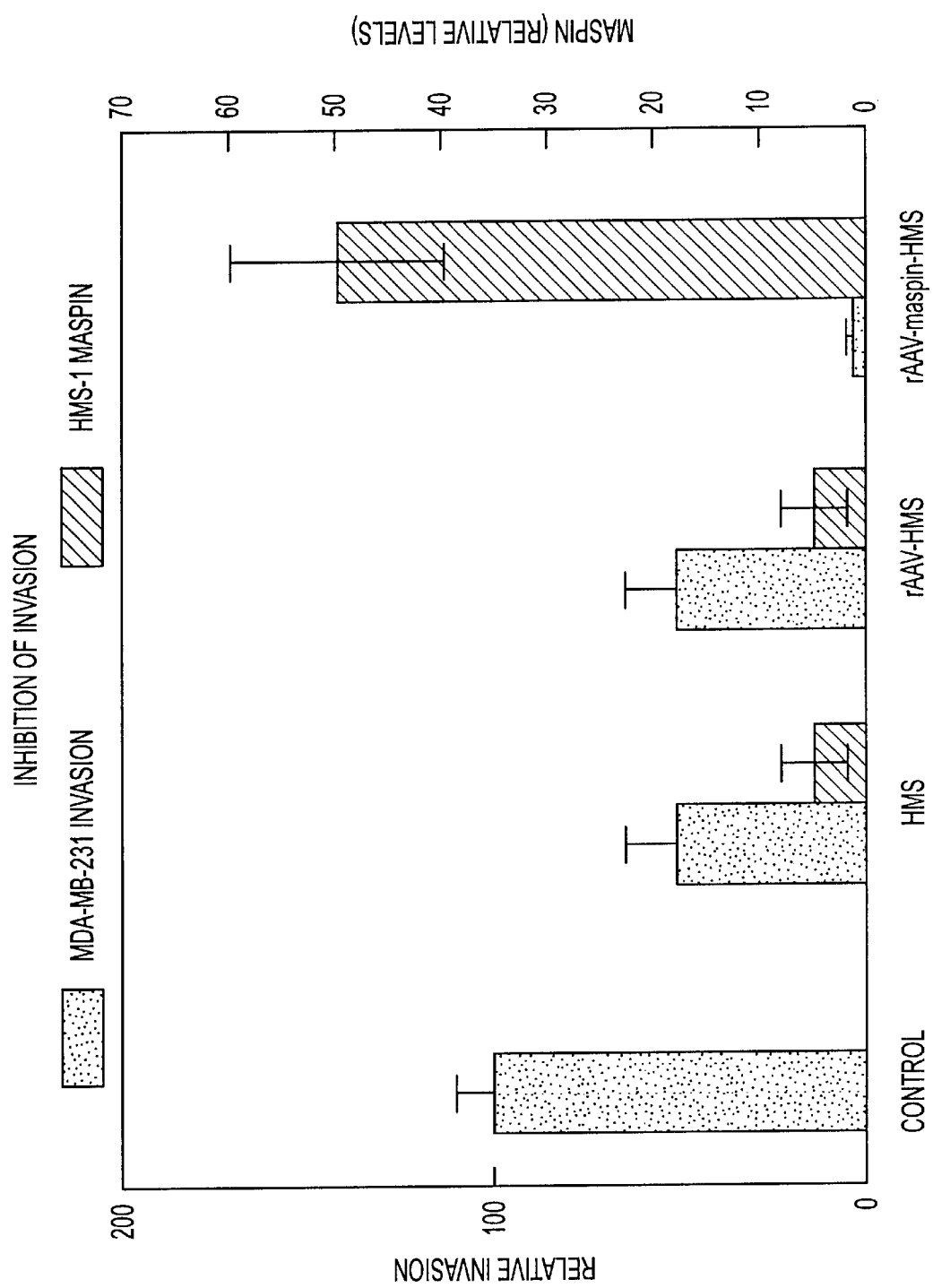
FIG. 7 is a bar graph comparing MDA-MB-231 breast carcinoma cell invasion in MATRIGEL matrix in the presence of no myoepithelial cells (control), HMS myoepithelial cells (HMS), rAAV transfected HMS myoepithelial cells (rAAV-HMS) and rAAV-recombinant maspin transfected HMS myoepithelial cells (rAAV-maspin-HMS). The results demonstrate that myoepithelial cells which overexpress maspin are highly effective at blocking carcinoma cell invasion in MATRIGEL matrix. Specifically, the effects of transfected myoepithelial clones expressing recombinant maspin in invasion inhibition assays show a 200% increase in inhibition of invasion.

Myoepithelial cells seem to have the unique ability to secrete this serpin. Therefore we exploited this property of myoepithelium by transfecting rmaspin into HMS-1 via rAAV in vitro to achieve maspin overexpression. rAAV containing the CMV promoter, for example, was used to modulate a full length maspin cDNA bgated into this vector. Levels of secreted rmaspin were determined by Western blot after several weeks. As shown in FIG. 7, myoepithelial cells overexpressing maspin are more effective at blocking carcinoma cell invasion in MATRIGEL matrix. Such MATRIGEL matrix assays are well known in the art and provide a model for breast cancer systems (see e.g. Bae et al., Breast Cancer Res. Tret. 24(3): 241–55 (1993). Specifically, the effects of transfected myoepithelial clones expressing rmaspin in invasion inhibition assays show a 200% increase in inhibition of invasion. Consequently, these results demonstrate the feasibility of using the overexpression of maspin in myoepithelial as an in vivo gene therapy strategy.

Example 5

In Vivo Studies

The ex vivo findings discussed in Examples 1–4 above illustrate how one can, using an intraductal approach, selectively target and destroy breast epithelium in vivo yet spare the underlying myoepithelium with rAd and/or alternatively selectively target the myoepithelium in vivo with rAAV and bolster its defense with genes such as maspin.

Specifically, using the preliminary ex vivo and in vivo studies disclosed herein, one can selectively target breast myoepithelium and breast epithelium with these vector-specific approaches. Therefore one can proceed in the following manner: use a replication-competent lytic adenovirus or a replication-competent lytic adenovirus containing cis elements which stimulate replication when specific trans factors present in breast epithelium are encountered (a candidate cis element would be the lactoalbumin promoter or the MUCI promoter). One can then evaluate the destruction of breast epithelium at risk for developing cancer and in effect perform a "prophylactic mastectomy" without having to remove the breast. Whether the myoepithelial layer would serve as an effective barrier against systemic infection when a replication-competent lytic adenovirus virus is used can be determined by urine and feces ELISA. The resistance of myoepithelial cells to adenovirus infection makes it likely that this layer offers a defense against systemic infection. Alternatively one can use rAAV to selectively target myoepithelium and deliver to it a candidate gene such as maspin to bolster its defensive abilities.

What is claimed is:

1. A method of selectively transducing a cell within a mixed population of ductal epithelial and myoepithelial cells, comprising the step of contacting the cell with a cell specific vector that transduces the cell through a coxsackie-adenovirus receptor molecule expressed by the ductal epithelial cell or a heparin sulfate proteoglycan molecule expressed by the myoepithelial cell, wherein the cell is a myoepithelial cell.

2. The method according to claim 1 wherein the vector is a recombinant adeno-associated virus.

3. The method according to claim 1, wherein the vector comprises a gene encoding a polypeptide which inhibits the proliferation of cells.

4. The method according to claim 3, wherein a control sequence in the recombinant adeno-associated virus contains a cis element which modulates the expression of the gene in the presence of a trans factor present in the myoepithelial cell.

5. The method according to claim 3, wherein the polypeptide inhibits the proliferation of a ductal epithelial cell.

6. The method according to claim 3, wherein the polypeptide inhibits the invasion of a ductal epithelial cell.

7. The method according to claim 3, wherein the polypeptide inhibits endothelial migration.

8. The method according to claim 3, wherein the polypeptide inhibits angiogenesis.

9. The method according to claim 3, wherein the polypeptide increases the production of nitric oxide by the myoepithelial cell.

10. The method according to claim 3, wherein the polypeptide induces apoptosis in a ductal epithelial cell.

11. The method according to claim 3, wherein the polypeptide is selected from the group consisting of maspin, thrombospondin-1, TIMP-1, protease nexin-II, α-1 antitrypsin and soluble bFGF receptor.

12. A method of selectively transducing a myoepithelial cell within a mixed population of ductal epithelial and myoepithelial cells in a ductal system in a mammary gland, comprising the step of contacting, by ductal cannulation, the cell with a vector that targets a heparin sulfate proteoglycan molecule expressed by the cell.

\* \* \* \* \*